(12) United States Patent
Khuon et al.

(10) Patent No.: US 9,314,610 B2
(45) Date of Patent: Apr. 19, 2016

(54) DEFIBRILLATION ELECTRODES

(75) Inventors: Pisit Khuon, Providence, RI (US);
Michael R. Dupelle, N. Attleboro, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 353 days.

(21) Appl. No.: 12/825,143

(22) Filed: Jun. 28, 2010

(65) Prior Publication Data

US 2011/0071611 A1 Mar. 24, 2011

Related U.S. Application Data

(63) Continuation-in-part of application No. 11/683,928, filed on Mar. 8, 2007, now Pat. No. 9,138,573.

(60) Provisional application No. 61/220,946, filed on Jun. 26, 2009.

(51) Int. Cl.
*A61N 1/04* (2006.01)
*A61N 1/39* (2006.01)

(52) U.S. Cl.
CPC .............. *A61N 1/046* (2013.01); *A61N 1/0492* (2013.01); *A61N 1/0476* (2013.01); *A61N 1/3906* (2013.01)

(58) Field of Classification Search
USPC ......................................... 607/4–5, 115, 142
See application file for complete search history.

(56) References Cited

U.S. PATENT DOCUMENTS

| 1,212,541 | A | | 1/1917 | Morse |
| 1,662,446 | A | | 3/1928 | Wappler |
| 3,972,329 | A | | 8/1976 | Kaufman |
| 4,092,985 | A | | 6/1978 | Kaufman |
| 4,633,879 | A | * | 1/1987 | Ong ............................... 600/391 |
| 4,653,501 | A | * | 3/1987 | Cartmell et al. ............... 600/392 |
| 4,674,512 | A | | 6/1987 | Rolf |
| 4,763,660 | A | * | 8/1988 | Kroll et al. ..................... 600/391 |
| 4,777,954 | A | * | 10/1988 | Keusch et al. ................. 600/392 |
| 4,779,630 | A | | 10/1988 | Scharnberg et al. |
| 4,838,273 | A | * | 6/1989 | Cartmell ........................ 600/385 |
| 5,111,812 | A | * | 5/1992 | Swanson et al. .................. 607/2 |
| 5,330,526 | A | * | 7/1994 | Fincke et al. .................. 607/142 |

(Continued)

FOREIGN PATENT DOCUMENTS

| CN | 201040143 | 3/2008 |
| WO | WO 93/21989 | 11/1993 |
| WO | WO 9321989 | * 11/1993 ............... A61N 1/04 |

OTHER PUBLICATIONS

"Biphasic Waveforms", IEEE Engineering in Medicine and Biology, Jun. 1990, p. 26.

*Primary Examiner* — Catherine Voorhees
*Assistant Examiner* — Roland Dinga
(74) *Attorney, Agent, or Firm* — Fish & Richardson P.C.

(57) ABSTRACT

A reusable component of a hands-free defibrillation electrode, the reusable component having a flexible nonconductive element, and a flexible metallic element supported by the flexible nonconductive element, wherein the flexible metallic element has an exposed surface on one side of the reusable component and the exposed surface is configured to be adhered to a disposable coupling portion, and wherein the reusable component is configured to accept an electrical defibrillation pulse and spread the electrical pulse across the exposed surface area, from which it is delivered to the patient's chest through the disposable coupling portion.

24 Claims, 12 Drawing Sheets

(56) References Cited

U.S. PATENT DOCUMENTS

| | | | |
|---|---|---|---|
| 5,356,428 A | 10/1994 | Way | |
| 5,427,096 A * | 6/1995 | Bogusiewicz et al. | 600/396 |
| 5,700,281 A | 12/1997 | Brewer et al. | |
| 5,769,872 A * | 6/1998 | Lopin et al. | 607/5 |
| 5,785,040 A | 7/1998 | Axelbaard | |
| 5,921,925 A * | 7/1999 | Cartmell et al. | 600/391 |
| 5,951,598 A | 9/1999 | Bishay et al. | |
| 6,019,877 A | 2/2000 | Dupelle et al. | |
| 6,076,002 A * | 6/2000 | Cartmell et al. | 600/372 |
| 6,101,413 A * | 8/2000 | Olson et al. | 607/5 |
| 6,115,638 A | 9/2000 | Groenke | |
| 6,280,463 B1 | 8/2001 | Dupelle et al. | |
| 6,564,079 B1 * | 5/2003 | Cory et al. | 600/393 |
| 6,587,726 B2 | 7/2003 | Lurie et al. | |
| 6,597,949 B1 | 7/2003 | Dhurjaty | |
| 6,714,824 B1 * | 3/2004 | Ohta et al. | 607/142 |
| 2003/0004558 A1 | 1/2003 | Gadsby | |
| 2003/0233129 A1 | 12/2003 | Matos | |
| 2004/0267325 A1 * | 12/2004 | Geheb et al. | 607/5 |
| 2005/0107834 A1 | 5/2005 | Freeman et al. | |
| 2005/0131465 A1 * | 6/2005 | Freeman et al. | 607/5 |
| 2006/0009809 A1 | 1/2006 | Marcovecchio et al. | |
| 2006/0074284 A1 | 4/2006 | Juola et al. | |
| 2006/0074452 A1 | 4/2006 | Dupelle et al. | |
| 2008/0221631 A1 * | 9/2008 | Dupelle | 607/5 |
| 2008/0312709 A1 | 12/2008 | Volpe et al. | |

* cited by examiner

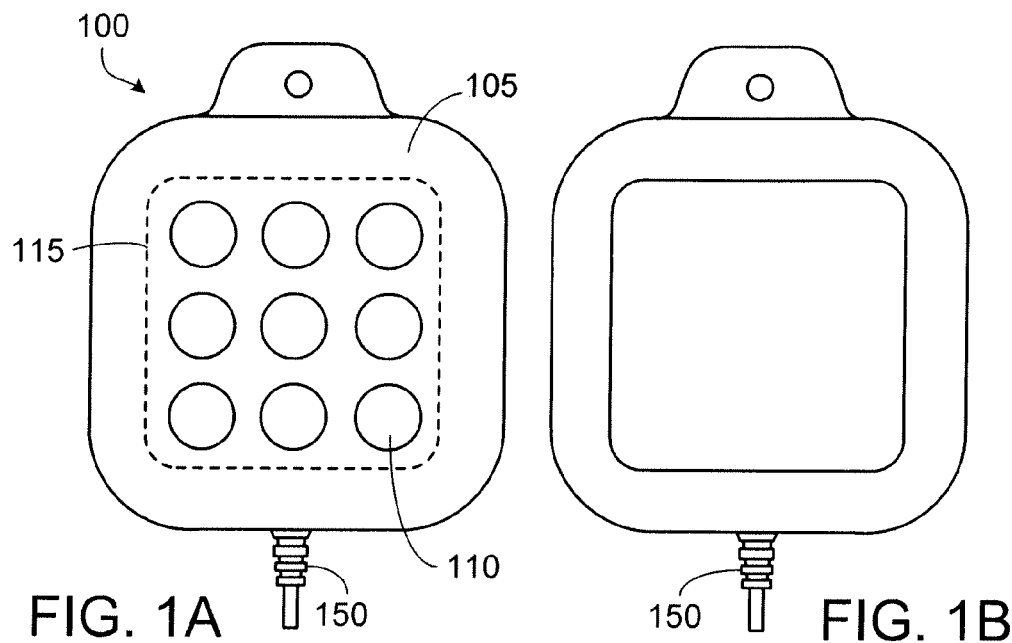
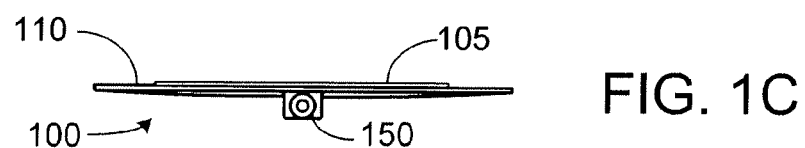
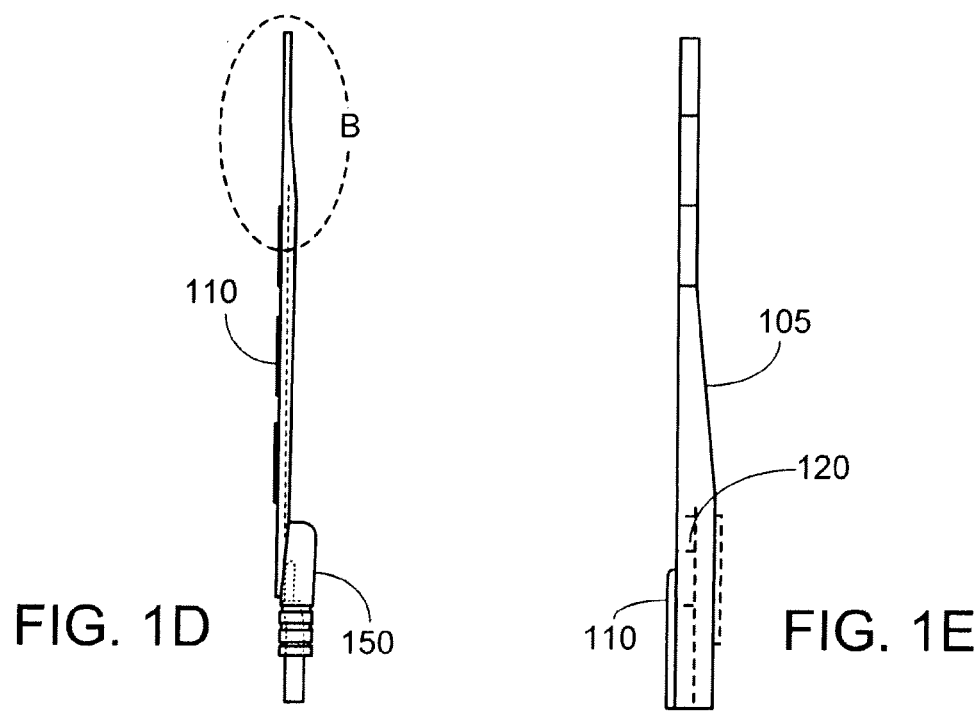

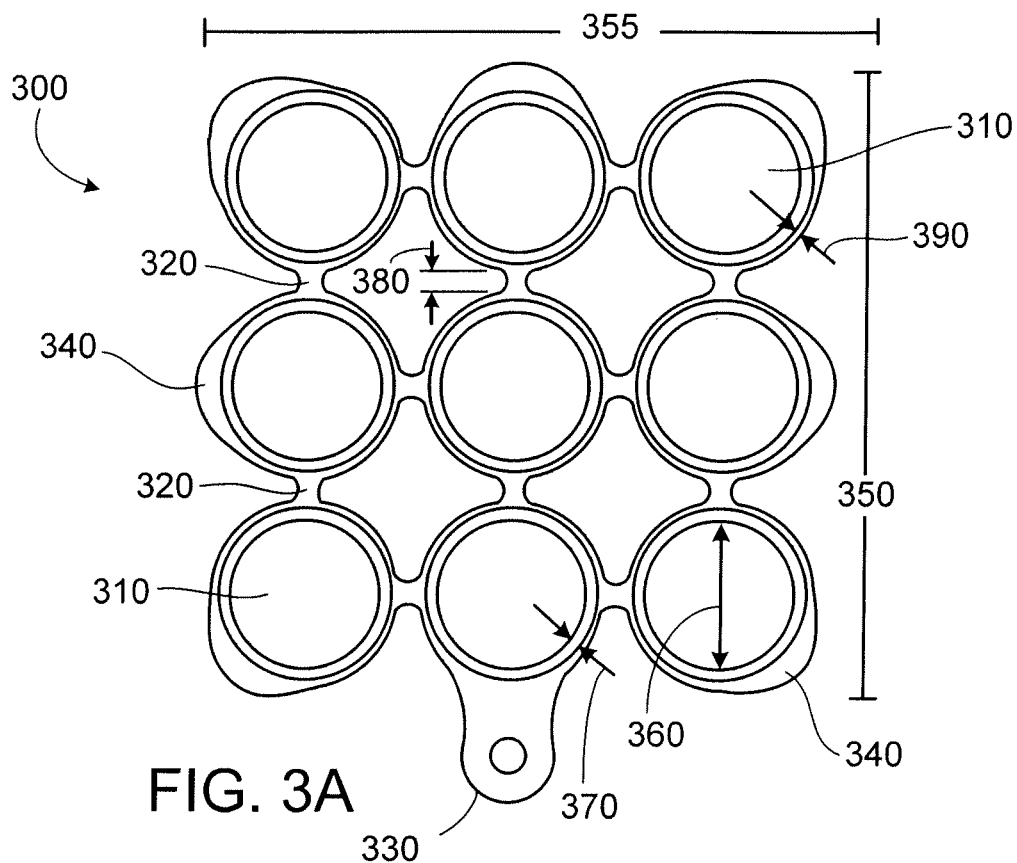
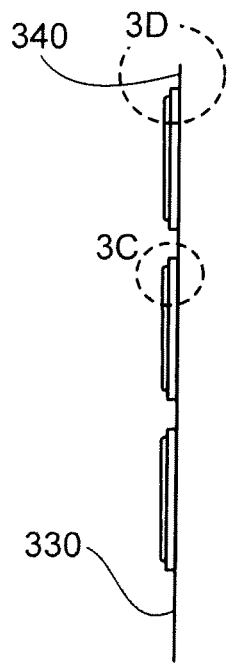 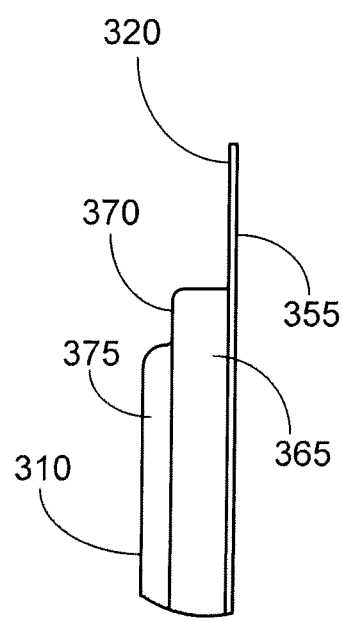 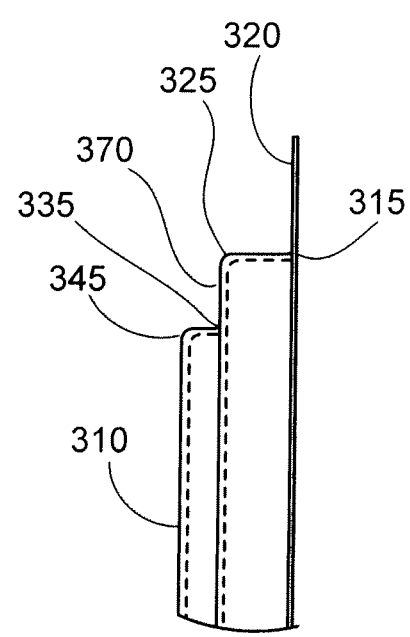
FIG. 3B    FIG. 3D    FIG. 3C

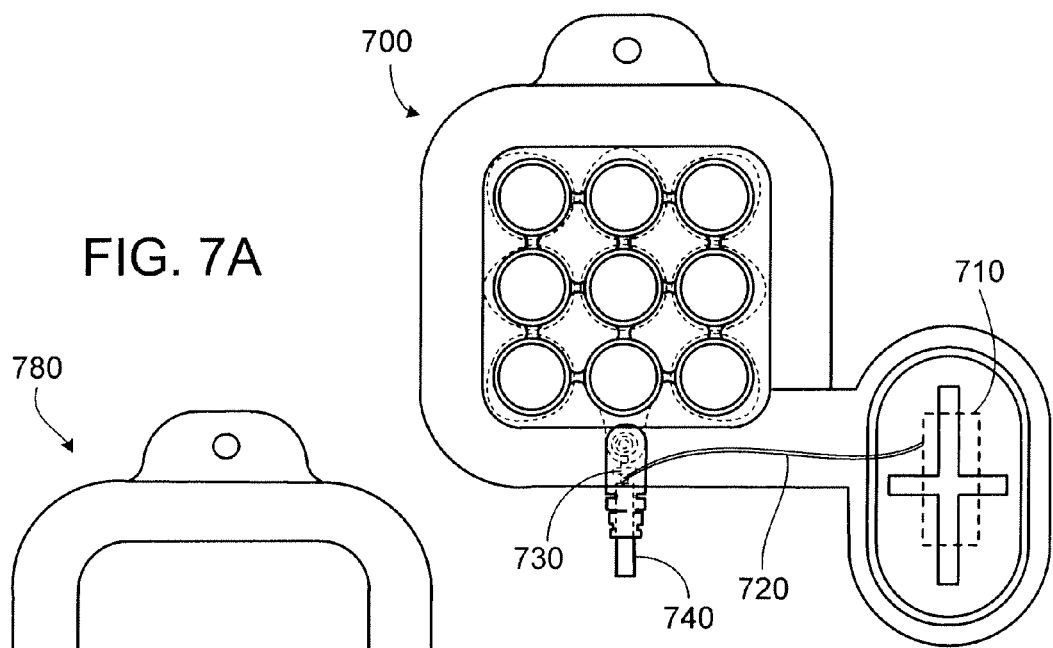
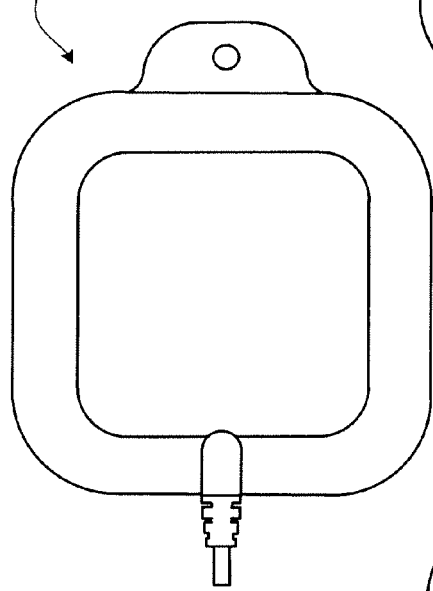
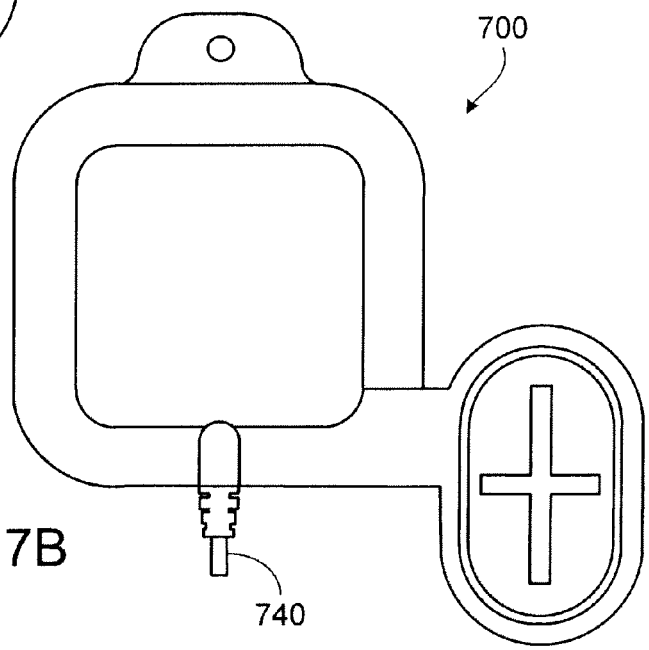
FIG. 7A
FIG. 7C
FIG. 7B

DEFIBRILLATION ELECTRODES

CROSS-REFERENCE TO RELATED APPLICATIONS

This application is a continuation-in-part application of and claims priority to U.S. application Ser. No. 11/683,928, filed on Mar. 8, 2007 now U.S. Pat. No. 9,138,573. This application also claims priority to U.S. Provisional Application Ser. No. 61/220,946, filed on Jun. 26, 2009. Both applications are hereby incorporated by reference.

TECHNICAL FIELD

This application relates to the construction of "hands-free" defibrillation electrodes.

BACKGROUND

External defibrillators frequently include a pair of "hands-free" disposable electrodes, which are essentially flexible pads that are adhered to the skin of a patient having a cardiac event (i.e., used transcutaneously). By "hands-free," we mean electrodes of the type that are adhered to a patient, rather than paddles that are held by a rescuer during defibrillation. Hands-free disposable electrodes typically include a nonconductive backing layer, a conductive metal layer, formed from a thin sheet of metal (e.g. tin or silver) or a conductive ink (e.g. silver-chloride) printed on a substrate, and a liquid or solid electrically conductive gel covering the metal layer so that electrical current passes through the gel to the patient's body. The area of contact between the gel and the patient's body where current is delivered is referred to herein as the "treatment area". Because such electrodes use a thin sheet of metal, flexibility is limited and cracking results from repeated use. Wire mesh or expanded metal have been proposed as a solution to this problem, but wire mesh provides for extraneous "noise" in ECG monitoring and expanded metal is also prone to cracking. Metal cracking results in arcing or failure to deliver therapy as required. As a result such typical electrodes are not reusable, requiring purchase of electrodes after use and consequently, increased costs.

External defibrillators also routinely use paddle electrodes, such as disclosed in Scharnberg U.S. Pat. No. 4,779,630. These paddle electrodes are not "hands-free". Typically, the rescuer applies a liquid gel to the metallic surface of the paddles, and presses the gelled surface against the chest of the patient during delivery of the defibrillation shock. Scharnberg also discloses an alternative construction in which disposable, gel-containing pads are secured to the metallic surface of the paddles. But the paddles with attached pads must still be held against the chest by the rescuer.

One important property of electrodes is that the material used in the metal layer depolarize quickly (within seconds) after a defibrillating pulse ("shock") is delivered to a patient. Otherwise, the electrode is not capable of sensing a signal that will allow the defibrillator to generate a clear ECG and determine whether another shock should be delivered within a short period of time.

US Patent Application Publication No. 2008/0221631, the disclosure of which is herein incorporated by reference, discloses that stainless steel, and other metals that polarize during a defibrillating pulse, can be used as the conductive metal layer in a defibrillating electrode, provided that the defibrillator with which the electrode is used is configured to deliver to the patient a defibrillation waveform that is capable of rapidly depolarizing the electrode. Stainless steel is an advantageous material for the conductive layer, as it is resistant to corrosion, thereby providing a long electrode shelf life. Stainless steel is also strong, and thus its use in the conductive layer reduces the likelihood that the electrode will be damaged by mishandling.

Such depolarizing waveforms include biphasic waveforms, e.g., those which are discussed in detail in U.S. Pat. No. 5,769,872, the disclosure of which is incorporated herein by reference. As disclosed in the earlier application, it is believed that the negative phase of a biphasic waveform reduces or eliminates the electrical charge, allowing the electrode to rapidly depolarize after the defibrillating pulse is delivered.

SUMMARY

In a first aspect, the invention features a reusable component of a hands-free defibrillation electrode, the reusable component comprising a flexible nonconductive element, and a flexible metallic element supported by the flexible nonconductive element, wherein the flexible metallic element has an exposed surface on one side of the reusable component and the exposed surface is configured to be adhered to a disposable coupling portion, and wherein the reusable component is configured to accept an electrical defibrillation pulse and spread the electrical pulse across the exposed surface area, from which it is delivered to the patient's chest through the disposable coupling portion.

Preferred implementations of this aspect of the invention may incorporate one or more of the following. The reusable component may be combined with a flexible disposable coupling portion, wherein the flexible disposable coupling portion may comprise a conductive layer configured to be in electrical contact with the chest of the patient on one of its surfaces and in electrical contact with the exposed surface of the metallic element of the reusable component on the other of its surfaces. The reusable component and disposable portion may be configured to be stored as separate elements, and may be adhered together when used to defibrillate a patient. The reusable component and disposable portion when adhered together may form an electrode capable of being flexed simultaneously in more than one direction of curvature in order to conform to the shape of the patient's chest. The flexible metallic element may comprise a plurality of substantially inflexible metallic elements interconnected by flexible metallic linking elements, and wherein the flexible metallic linking elements may be narrower than the substantially inflexible metallic elements, and wherein the majority of the flexibility of the metallic element may be provided by flexure of the narrower flexible metallic linking elements. The substantially inflexible metallic elements and flexible metallic linking elements may be cut from the same sheet of metal. The flexible metallic element may be made from stainless steel. The flexible metallic element may be made from stainless steel. The flexible metallic element may be encapsulated by the flexible nonconductive element by molding the flexible nonconductive element around portions of the flexible metallic element. The flexible metallic element may be encapsulated by the flexible nonconductive element by molding the flexible nonconductive element around portions of the flexible metallic element. The flexible nonconductive element may comprise an elastomeric material. The conductive layer of the coupling portion may comprise a conductive viscous liquid. The conductive viscous liquid may comprise an electrolyte. The conductive layer of the coupling portion may comprise a solid conductive gel. The conductive layer may comprise hydrogel. The disposable coupling portion may include a first peripheral adhesive region configured to adhere to the periphery of the reusable component. The disposable coupling portion may include a second peripheral adhesive region on the surface opposite the surface carrying the first peripheral adhesive region, and the second peripheral adhesive region may be configured to adhere to the chest of the patient. The first and second peripheral adhesive regions may be generally peripherally outside of the area through which electrical current flows from the exposed surface of the reusable component through the conductive layer of the coupling portion to the chest of the patient. The conductive layer of the coupling portion may comprise a solid conductive gel with adhesive properties sufficient to adhere the coupling portion to the chest of the patient. The electrode may further comprise first and second release liners that, prior to assembly of the coupling portion to the reusable component, cover the first and second peripheral adhesive regions, respectively. The electrode may further comprise first and second release liners, and wherein, prior to assembly of the coupling portion to the reusable component, the first release liner may cover the first peripheral adhesive region and the second release liner may cover the solid conductive gel. The reusable component may be combined with a sensor that provides an output from which information about the depth of CPR chest compressions can be obtained. The sensor may comprise an accelerometer. The reusable component may be combined with a sensor that provides an output from which information about the force applied to the chest during CPR chest compressions can be obtained. The reusable component may be combined with a sensor that provides an output from which information about the rate of CPR chest compressions can be obtained. The exposed surface of the metallic element may comprise exposed portions of each of the inflexible metallic elements. The metallic linking elements may be fully encapsulated within the nonconductive element so that the exposed surface comprises a plurality of exposed metallic areas separated by nonconductive areas. Each of the plurality of exposed metallic areas may project beyond the surface of the surrounding nonconductive element.

In other aspects of the invention, an electrode may comprise a composite structure, wherein the composite structure comprises a conductive metal component that is partially encapsulated in a non-conductive matrix. The electrode may further comprise a coupling layer. The non-conductive matrix may be flexible. The non-conductive matrix may be an elastomer. The non-conductive matrix may be selected from the group consisting of rubbers, silicone rubber, synthetic rubbers, polychloroprene, thermoplastic elastomers and thermoplastic vulcanizates. The conductive metal component may be comprised of a metal selected from the group consisting of stainless steel alloys, tin, silver, silver chloride, aluminum and copper. Stainless steel alloys may be selected from the group consisting of 302, 316 and 316L. The conductive metal component may be flexible. The conductive metal component may comprise an array of two or more plates connected to each other by bridges. The conductive metal component may comprise a three by three array of nine plates connected to each other by bridges. The plates may be substantially inflexible. The bridges may be flexible. The electrode may be a medical electrode. The portions of the conductive metal component that are not encapsulated by the non-conductive matrix may be on the surface of the electrode that faces a patient. The portions may be planar or circular or both. The portions may project beyond the surface of the non-conductive surface. The treatment area associated with the electrode may be at least 15 sq. cm. The combined treatment area of an apex electrode and a sternum electrode when used in combination may be at least 45 sq. cm. The treatment area associated with the electrode may be at least 50 sq. cm. The combined treatment area of an apex electrode and a sternum electrode when used in combination may be at least 150 sq. cm. The metal component may be connected to an external source of electrical current. The portions of the conductive metal component that are not encapsulated may be circular in shape. The conductive metal component may be comprised of a single stamped component. The coupling layer may be comprised of an electrolyte. The coupling layer may be comprised of a hydrogel. The composite structure may be reusable. The coupling layer may be disposable. The coupling layer may be releasably attached to the composite structure. The coupling layer may comprise a hydrogel that may be attached around its perimeter to an adhesive ring. The adhesive ring may be attached to the composite structure outside of the treatment area. The coupling layer may be configured to be adhered to the skin of a patient. The coupling layer may be packaged between two releasable liners prior to attachment to the composite structure. The electrode may be configured for one or more of defibrillation, electrical signal monitoring, ECG monitoring, cardiac pacing and cardioversion. The coupling layer may include an additional metallic layer in order to enable cardiac pacing. The portions of the conductive metal that are not encapsulated by the non-conductive matrix may be in a 3 by 3 array. The electrode may be attached to a sensor constructed to acquire data indicative of the depth and rate of CPR compressions. The sensor may be an accelerometer or one or more of force and pressure monitors. The data may be processed by a defibrillator to provide CPR feedback.

In still other aspects of the invention, the electrode may have a reusable component. The reusable component may comprise a composite structure, wherein the composite structure comprises a conductive metal component that is partially encapsulated in a non-conductive matrix. The non-conductive matrix may be flexible. The non-conductive matrix may be an elastomer. The non-conductive matrix may be selected from the group consisting of rubbers, silicone rubber, synthetic rubbers, polychloroprene, thermoplastic elastomers and thermoplastic vulcanizates. The conductive metal component may be comprised of a metal selected from the group consisting of stainless steel alloys, tin, silver, silver chloride, aluminum and copper. Stainless steel alloys may be selected from the group consisting of 302, 316 and 316L. The conductive metal component may be flexible. The conductive metal component may comprise an array of two or more plates connected to each other by bridges. The conductive metal component may comprise a three by three array of nine plates connected to each other by bridges. The plates may be substantially inflexible. The bridges may be flexible. The electrode may be a medical electrode. The portions of the conductive metal component that are not encapsulated by the non-conductive matrix may be on the surface of the electrode that faces a patient. The portions may be planar or circular or both. The portions may project beyond the surface of the non-conductive surface. The treatment area associated with the electrode may be at least 15 sq. cm. The combined treatment area of an apex electrode and a sternum electrode when used in combination may be at least 45 sq. cm. The treatment area associated with the electrode may be at least 50 sq. cm. The combined treatment area of an apex electrode and a sternum electrode when used in combination may be at least 150 sq. cm. The metal component may be connected to an external source of electrical current. The portions of the conductive metal component that are not encapsulated may be circular in shape. The conductive metal component may be comprised of a single stamped component. The reusable component may further be used with a disposable component which comprises a coupling layer. The coupling layer may be comprised of an electrolyte. The coupling layer may be comprised of a hydrogel. The coupling layer may be releasably attached to the composite structure. The coupling layer may comprise a hydrogel that may be attached around its perimeter to an adhesive ring. The adhesive ring may be attached to the composite structure outside of the treatment area. The coupling layer may be configured to be adhered to the skin of a patient. The coupling layer may be packaged between two releasable liners prior to attachment to the composite structure. The electrode may be configured for one or more of defibrillation, electrical signal monitoring, ECG monitoring, cardiac pacing and cardioversion. The coupling layer may include an additional metallic layer in order to enable cardiac pacing. The portions of the conductive metal that are not encapsulated by the non-conductive matrix may be in a 3 by 3 array. The electrode may be attached to a sensor constructed to acquire data indicative of the depth and rate of CPR compressions. The sensor may be an accelerometer or one or more of force and pressure monitors. The data may be processed by a defibrillator to provide CPR feedback.

In another aspect of the invention, the electrode may be configured to be used as a "hands-free" electrode and to deliver a defibrillating pulse to the patient. In alternative implementations, electrodes are configured to also monitor electrical signals from the patient's body, and to deliver a defibrillating pulse comprising a waveform configured to substantially depolarize the metal. By "substantially depolarize," we mean that polarization is eliminated, or reduced sufficiently so that a clear ECG can be read by the defibrillator.

Other features and advantages of the invention will be found in the detailed description, drawings, and claims.

BRIEF DESCRIPTION OF DRAWINGS

FIGS. 1A-1E are front, back and side views of a composite electrode structure in accordance with one implementation of the invention.

FIGS. 3A-3I are illustrations of various aspects of a conductive metal component (including the ability of the component to be flexed simultaneously in more than one direction of curvature in order to conform to the shape of the body).

FIGS. 7A-7C are illustrations of electrodes in an alternative implementation of the invention, in which a sensor is incorporated into the electrode assembly.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

As discussed above, a hands-free electrode typically includes a non-conductive backing layer, a conductive layer, formed from a thin sheet of metal or a conductive ink printed on a substrate, and a coupling layer, typically liquid or solid electrically conductive gel or other electrolytic material, covering the metal layer so that electrical current passes through the gel (or other electrolyte) to the patient's body. A lead connecting the electrode to a defibrillator is also included. It is well known that defibrillators utilize two electrodes, commonly referred to as sternum and apex electrodes.

The implementation of the electrode disclosed below differs from the electrode described above in that it includes a reusable component having a composite structure comprising a conductive metal component that is partially encapsulated in a non-conductive matrix material (e.g., by molding the non-conductive material around at least portions of the conductive metal component). A disposable coupling portion is adhered to the reusable component to form the hands-free electrode for delivering defibrillation currents to a patient.

Figure 3E:
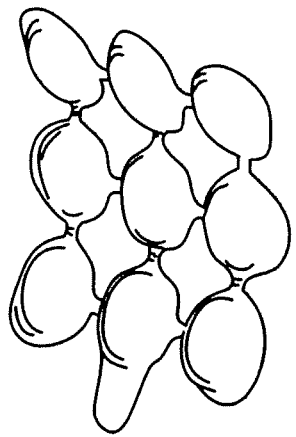
Figure 3F:
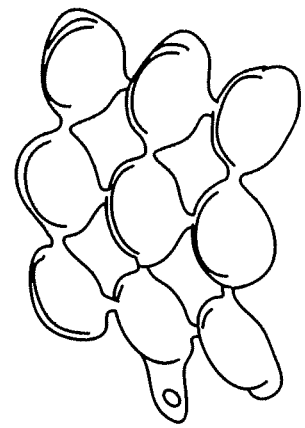
Figure 3G:
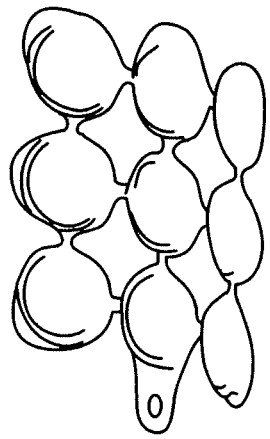
Figure 3H:
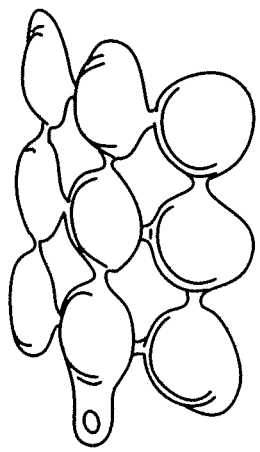
Figure 3I:
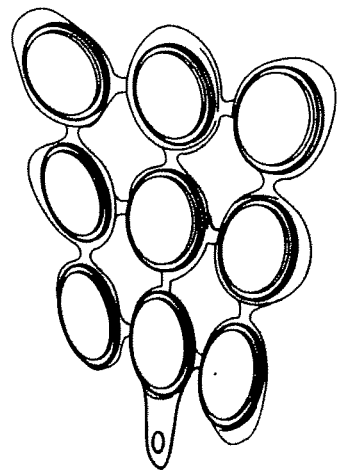

FIGS. 1A-1E shows one implementation of a composite structure noted above. In FIG. 1A, the composite structure 100 includes an electrically non-conductive matrix 105 (one implementation of the "flexible nonconductive element" referred to elsewhere) that encapsulates a portion of a conductive metal component. The composite structure has an encapsulated high voltage lead 150 for connection to an electrical source such as a defibrillator. The lead may connect via an eyelet or other connecting means as discussed below to the metal component. The conductive metal component will be described separately in further detail below. Those portions 110 of the metal component not encapsulated in the matrix are on the top surface (the patient side) of the composite structure and deliver electrical current to a patient via an electrolyte or other conductive viscous liquid (not shown) that is between the composite structure and a patient. Accordingly, these portions 110 may be referred to herein as the "exposed surfaces" or "current delivery surfaces". The contact area of a current delivery surface may be inflexible and the uppermost surface may be planar. The composite structure is configured such that the treatment area (exemplified by the area 115 within the dotted line in FIG. 1A) is may be at least 2.33 sq. inches (15 sq. cm), with a combined treatment area associated with two electrodes (the sternum electrode and the apex electrode) of 6.98 sq. inches (45 sq. cm) for pediatric electrodes; and 7.75 square inches (50 square cm), with a combined treatment area associated with two electrodes (the sternum electrode and the apex electrode) of at least 23.25 square inches (150 square cm) for all other electrodes, in accordance with AAMI DF-80 and international requirements. In a preferred implementation the treatment area associated with each pediatric electrode is 7.56 sq. inches (22.5 sq. cm) and for all other electrodes 11.63 square inches (75 square cm.) per electrode. The area outside of the treatment area 115 (which is comprised of the non-conductive matrix) should be of sufficient dimensions as to prevent lateral discharge of current to the outer edge of the electrode and to enable attachment of an adhesive ring to which a coupling layer such as hydrogel is attached. As can be seen in FIG. 1B, which shows the bottom surface of the composite structure (opposite the patient side), the conductive metal component is completely covered with the non-conductive material of sufficient thickness such that no electrical current passes through the bottom surface. FIG. 1C shows an end-on side view of the composite structure. FIG. 1D shows a side view of the composite structure. FIG. 1E shows an expanded view of circled section B in FIG. 1D. As can be seen (and will be discussed in greater detail below), the current delivery surfaces 110 of the composite structure 100 may protrude beyond the surface of the non-conductive matrix 105. As can be seen by the dashed lines in FIGS. 1D and 1E (in expanded detail), the conductive metal component 120 (described in greater detail below) may be partially embedded in the non-conductive matrix 105. The portion of the current delivery surface that extends beyond the surface of the non-conductive matrix corresponds to step 375 (shown in FIG. 3D). Thus non-conductive matrix may extend up to the top of step 365 (shown in FIG. 3) or as shown by indicia 120.

Alternative dimensions (length and width) for the metal component, treatment area and composite structure are set forth below. It is noted that these dimensions reflect composite structures (as well as metal components) with equal length and width, which is preferred for manufacturing and packaging. However, the invention is not limited to such dimensions, and is applicable to electrodes of any dimension (whether or not the length and width are equal) or shape (e.g. circular, oval, rectangular or other shapes well known in the art), provided that the treatment area is sufficiently large for defibrillation or cardioversion and the minimum treatment area standards noted in AAMI DF-80 and required by regulation are met. For example instead of having an electrode configured for a treatment area that is 2 inches by 2 inches, the electrode could be configured for a treatment area that is one inch by four inches. Of course the apex and sternum electrodes may be of dissimilar size and shape.

Table 1 shows non-limiting examples of possible dimensional ranges (length and width) for pediatric electrodes and Table 2 shows non-limiting examples of possible dimensions ranges (length and width) for other, non-pediatric, electrodes.

TABLE 1

| | Pediatric Electrode - Dimensional Range (inches) | | | | |
|---|---|---|---|---|---|
| | Preferred | | More Preferred | | Still More |
| | Min | Max | Min | max | Preferred |
| Metal Component | 1.5 × 1.5 | 3 × 3 | 2 × 2 | 3 × 3 | 2.5 × 2.5 |
| Treatment Area | 2 × 2 | 3.5 × 3.5 | 2.5 × 2.5 | 3 × 3 | 2.75 × 2.75 |
| Composite Structure | 2.5 × 2.5 | 5 × 5 | 3 × 3 | 4 × 4 | 3.5 × 3.5 |

TABLE 2

| | Non-pediatric Electrode - Dimensional Range (inches) | | | | |
|---|---|---|---|---|---|
| | Preferred | | More Preferred | | Still More |
| | min | max | Min | Max | Preferred |
| Metal Component | 3 × 3 | 4 × 4 | 3 × 3 | 3.5 × 3.5 | 3 × 3 |
| Treatment Area | 3.5 × 3.5 | 4.5 × 4.5 | 3.5 × 3.5 | 4 × 4 | 3.5 × 3.5 |
| Composite Structure | 4 × 4 | 7.5 × 7.5 | 5 × 5 | 6 × 6 | 5 × 5 |

It is noted that the dimensions of the treatment area in any length and/or width direction is preferably not greater than the dimensions of the composite structure in those same one or more directions.

Table 3 below illustrates alternative thicknesses for the composite structure. The thickness of the structure should take into consideration at least the following: (a) the thickness of the non-conductive material should preferably be sufficient to prevent the passage of current (e.g. current only comes out of the electrode at the current delivery surfaces; (b) the electrode should preferably be thin enough to be flexible, yet thick enough to be durable; (c) the wall thickness should preferably be sufficiently thick for molding of the composite structure; and (d) sufficient surface area for the metal to bond to the non-conductive matrix. The thickness may taper to the outer edge of the composite structure.

TABLE 3

| | Dimensional Range (inches) | | | | |
|---|---|---|---|---|---|
| | Preferred | | More Preferred | | Still More |
| | Min | Max | Min | Max | Preferred |
| Thickness within Treatment Area | .063 | .250 | .094 | .188 | .125 |
| Thickness outside Treatment Area | .032 | .125 | .047 | .094 | .063 |

Figure 2A:
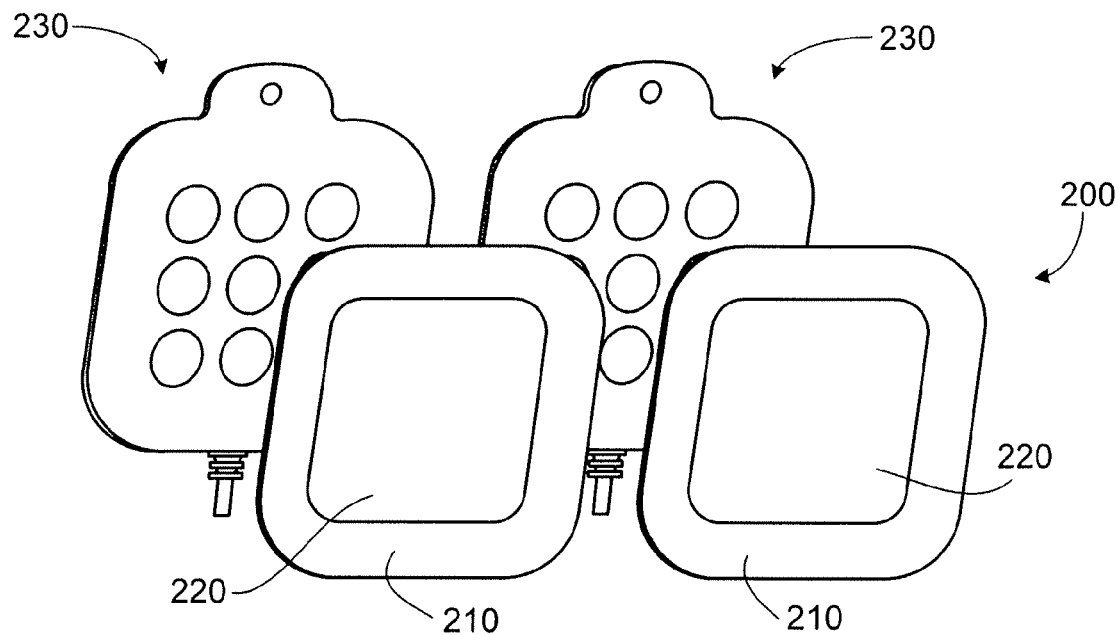
FIGS. 2A-2B are illustrations of how a coupling assembly can be attached to the composite structure.
Figure 2B:
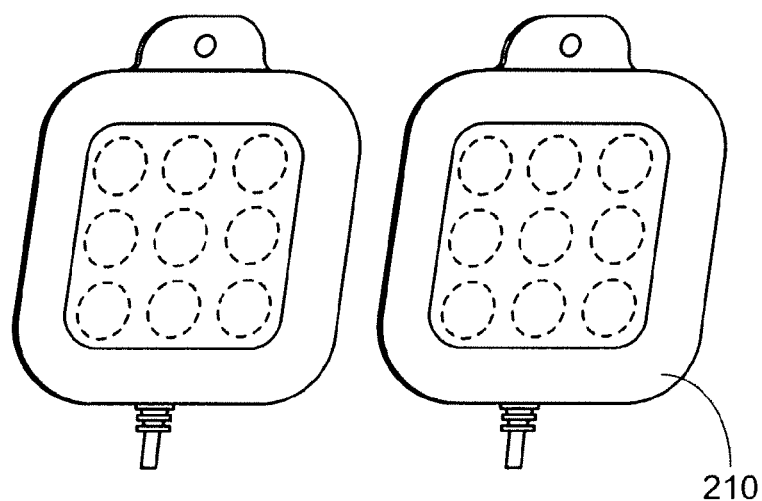

FIGS. 2A and 2B illustrate an implementation of the above described electrode that shows how the composite structure connects with a coupling layer. As shown in FIG. 2A (exploded view) coupling assembly 200 (one possible implementation of a "disposable coupling portion" referred to elsewhere), comprised of an adhesive ring 210 and containing hydrogel 220, may be adhered to composite structure 230. The assembled electrode structure is shown in FIG. 2B. The adhesive ring 210 may also include adhesive on a patient side for attachment of the electrode to a patient. It is noted that the coupling assembly 200 may be disposable, while the composite structure may be reusable, as will be discussed in greater detail below.

FIG. 3A shows an implementation of a structure of conductive metal component 300. Conductive metal component 300 includes nine circular plates 310 in a three by three array wherein each plate is connected via a metal bridge 320 (one possible implementation of a "metallic linking element" referred to elsewhere) to one or more adjacent plates. The dimensions 350, 355, 360, 370, 380 and 390 of the array are determined by the overall size of the electrode and the width of the area outside of the treatment area 115 (shown in FIG. 1A). The bridges may be flexible. An eyelet 330 may be attached to one or more of the plates or bridges. This eyelet allows for attachment of a high voltage lead for defibrillation, and in alternative implementations electrical signal monitoring, ECG monitoring, cardiac pacing and/or cardioversion. Flanges 340 may be added to the edges of the plates to increase the footprint of the metal embedded in the non-conductive matrix. FIG. 3B shows a side view of the array of FIG. 3A; with FIGS. 3C and 3D showing expanded versions of the encircled areas. As can be seen from FIGS. 3B-3D, the plates have a stepwise structure, with steps 365 and 375. While a single step could be used (resulting in the surface of the metal component being flush with the non-conductive surface), the use of multiple steps offers certain advantages such as improved attachment of the metal component to the non-conductive matrix (which can fill in the area under the metal component and the area between each plate (over the bridges) up to the top of step 365) and easier overmolding of the metal component with the non-conductive matrix. Step 375 allows the plate to protrude above the level of the nonconductive matrix which provides for improved contact with the coupling layer and improved fixation of the coupling layer to the composite over the treatment area. In particular, in certain aspects, the height of the second step (375) correlates with the thickness of the adhesive ring holding the coupling layer such that the surface of the coupling layer that is in contact with a patient is level, thus ensuring uniform current application across the treatment area.

In a non-limiting example, with reference to FIGS. 3A-3D, dimensions 355 and 350 are each three inches; dimension 360 (the diameter of a current delivery surface) is 0.813 inches (2.065 cm); dimension 370 is 0.063 inches (0.160 cm) and dimension 380 is 0.25 inches (0.635 cm). Dimensions 315, 325, 335, 345 and 355 which are the thickness of the metal at selected points on the array are equal to 0.005 (0.013 cm) inches. The height of step 365 is 0.063 inches (0.160 cm) and height of step 375 is 0.031 inches (0.787 cm).

FIGS. 3E-3I illustrate the flexibility of the three by three array metal component described above. As described above, flexibility of the metal component may be achieved via the flexibility of the bridges.

Figure 4A:
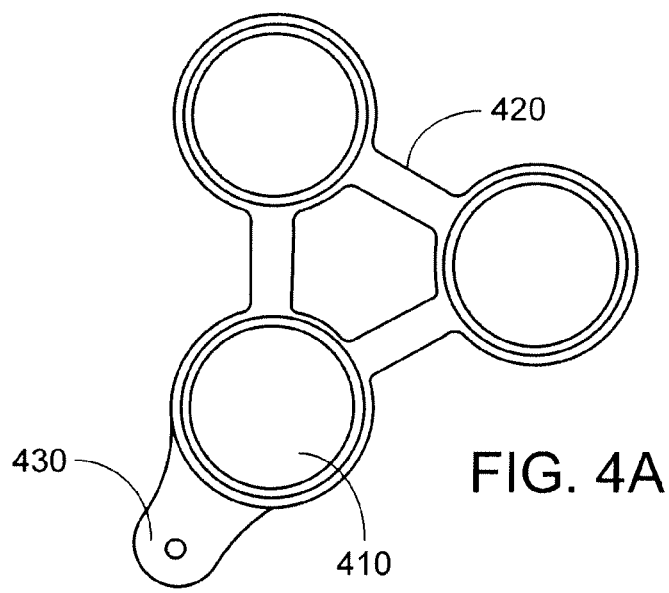
FIGS. 4A-4E are illustrations of various aspects of an alternative metal component.
Figure 4B:
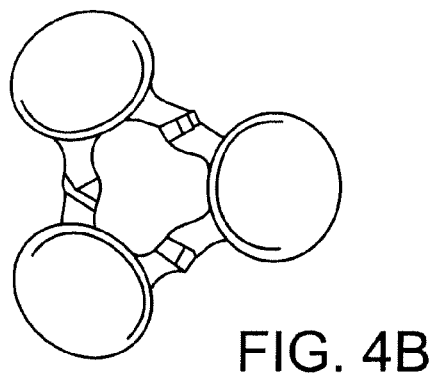
Figure 4C:
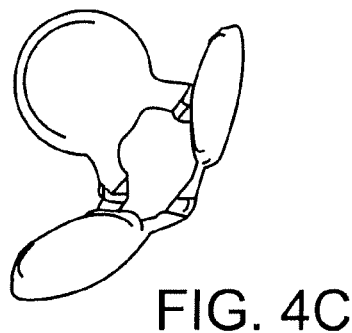
Figure 4D:
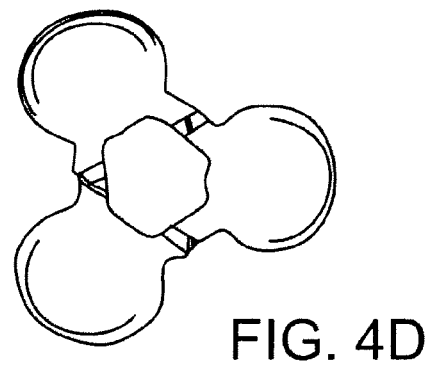
Figure 4E:
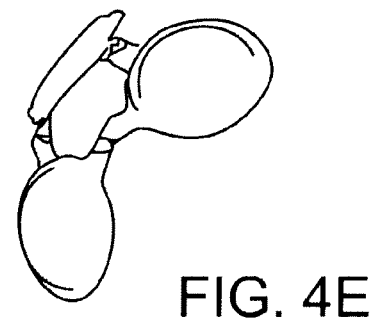

The metal component is not limited to the specific implementations described above, rather a metal component may have two or more current delivery surfaces. For example, FIG. 4A shows one implementation of a structure of conductive metal component 400 that includes three substantially inflexible circular plates 410 wherein each plate is connected via a metal bridge 420 to one or more adjacent plates. The bridges may be flexible. An eyelet 430 may be attached to one or more of the plates or bridges. This eyelet allows for attachment of a high voltage lead for defibrillation. In certain implementations, the same lead may be used for electrical signal monitoring, ECG monitoring, cardiac pacing and/or cardioversion. Other means of attaching leads for defibrillation, ECG monitoring, cardiac pacing and/or cardioversion may be utilized. Flanges may be added to the edges of the plates to increase the footprint of the metal in the non-conductive matrix.

FIGS. 4B-4E illustrate the flexibility of a conductive component having three plates. In these figures it can be seen that the flexibility derives from the bridges between the plates.

The thickness of the metal in the metal component may be on the order of 0.004-0.008 inches (0.010-0.020 cm). In one implementation the thickness is 0.005 inches (0.013 cm). The metal should be thick enough so as to provide durability and ease of manufacture, yet thin enough to allow flexibility of the composite structure sufficient to conform to a patient's body. The spacing between the plates should be close enough such that, when used in conjunction with a coupling layer, the lateral conductivity of the coupling layer produces a substantially uniform current distribution at the interface of the coupling agent and the patient's skin over the treatment area (e.g. the electrode "functions" as a single plate instead of as, for example with reference to FIG. 3A, nine distinct plates). As indicated above, the treatment area should have a surface area that is sufficiently large for defibrillation or cardioversion.

In one implementation, the metal component is comprised of stainless steel. Suitable stainless steel alloys include, for example, 302, 316, 316L and alloys having similar composition. Other metal alloys may be used. The metal component may also be made of tin, silver, aluminum, silver chloride, copper or other metal or metal combinations (e.g. silver coated copper), and may be in the form of a metallic or conductive ink (e.g. silver-chloride) disposed on a suitable substrate such as polyester, as known to those skilled in the art. In an alternative implementation, the metal component is comprised of any metal that polarizes during a defibrillation pulse is delivered. Where such a metal is used, it is preferred to use it in conjunction with a waveform that substantially depolarizes the electrode within 6 seconds of the delivery of the defibrillation pulse.

The metal component can be a single stamped piece and be annealed for flexibility and to minimize the presence of brittle joints. The use of a single stamped piece facilitates handling and overmolding and eliminates the need for welding or soldering of the bridges and/or plates. On the other hand, the component may be made of multiple plates that are welded or soldered together, or that are mechanically connected.

In another alternative implementation, wires can be connected directly to individual current delivery surfaces. This would lead to good flexibility of the composite structure, but would be more complex to manufacture. The wires could be arranged in a network to optimize connectivity by making redundant connections without compromising flexibility. The wires would be connected to the high voltage lead at a common node.

In another alternative implementation, a flexible circuit with a printed conductive element can be used instead of the metal component described above.

Figure 5A:
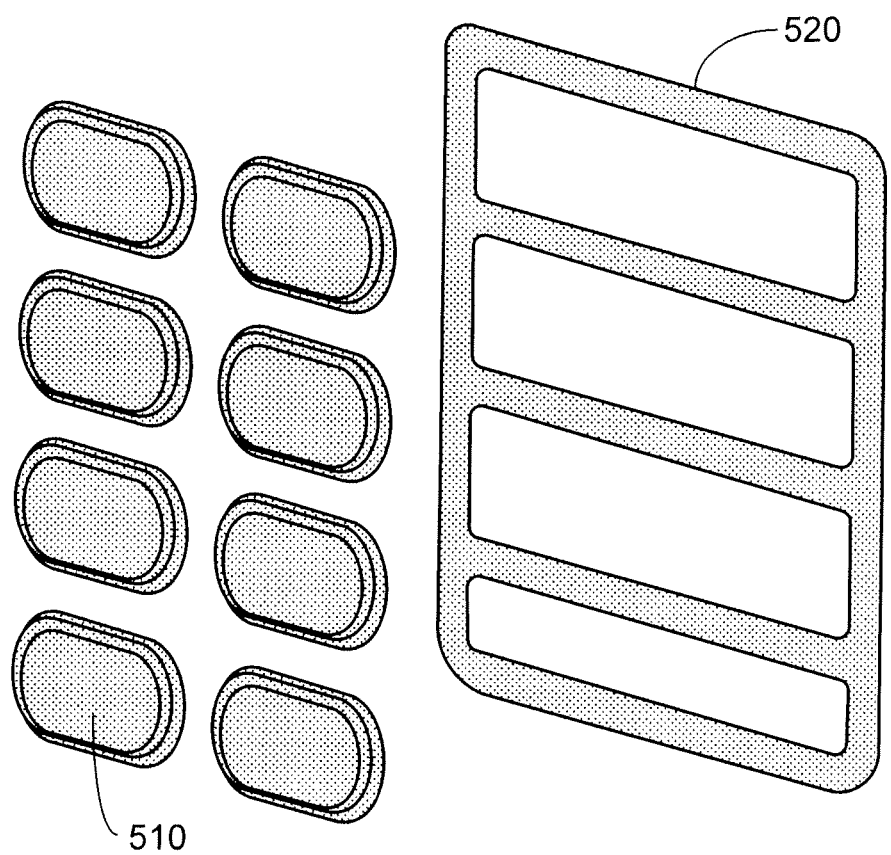
FIGS. 5A-5B are illustrations of an alternative metal component.
Figure 5B:
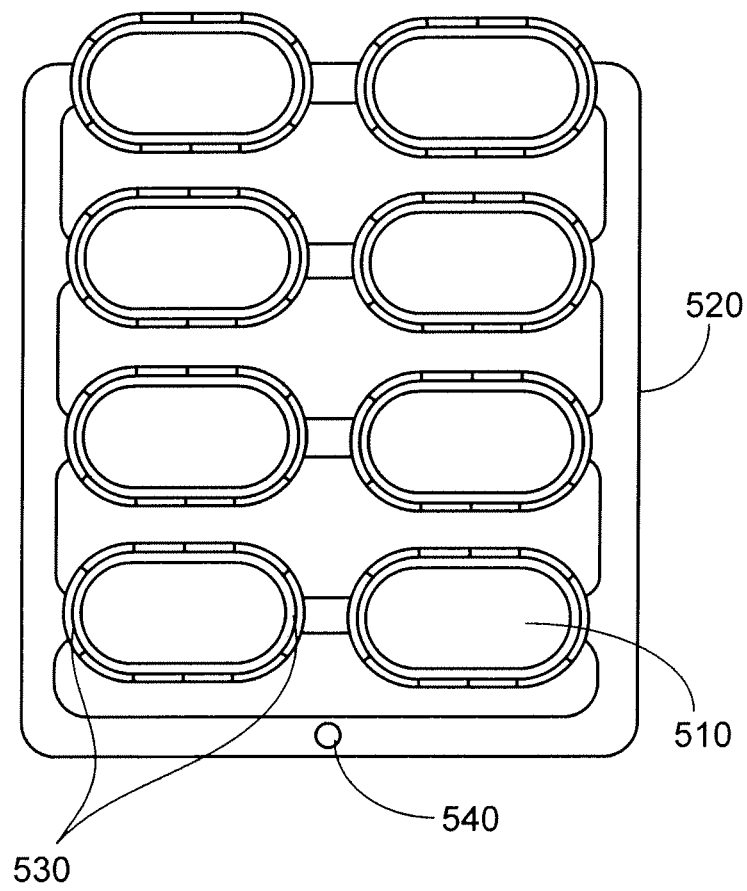

An additional implementation is illustrated in FIGS. 5A and 5B. As shown in FIG. 5B, individual (non-circular; though any shape may be used) conductive plates 510 are attached to a conductive backing layer 520 (that may be flexible) via attachment points 530. A connection point 540 for a wire connection to a defibrillator is within the conductive backing layer 520.

As indicated above, the metal component is partially encapsulated in an electrically non-conductive matrix. This may be accomplished by molding the metal component within an elastomer. Molding the metal component within an elastomer may be accomplished via any suitable process known to those skilled in the art. Such processes may include injection molding, overmolding and insert molding. The composite may also be made by sandwiching the metal component between two (or more) non-conductive matrix pieces, and adhering the non-conductive matrix pieces together. The metal may be passivated to remove any surface contamination, a heat activated adhesive (e.g. Chemlock 608, available from Lord Corporation, Cary, N.C., USA) is added to the metal at locations where the elastomer will be in contact with the metal, and an elastomer is bonded to the metal in a hot vulcanization process.

Any flexible elastomer or rubber may be utilized as the non-conductive matrix. These materials may have one or more of the following properties: flexibility, durability, resistance to chemicals such as cleaning and disinfecting materials (e.g. bleach, alcohol and gluteraldehyde), resistance to temperature extremes, biocompatibility (e.g. ISO 10993 compliant), and good adhesion to the metal. Such materials may include, but are not limited to silicone rubber (e.g. Class VI Elastomer C6-150, available from Dow Corning Corporation, Midland, Mich. USA), synthetic rubbers (e.g. Neoprene polychloroprene available from DuPont Performance Elastomers, Wilmington, Del., USA), thermoplastic elastomers (e.g. Sarlink plastics resins available from DSM Thermoplastic Elastomers, Inc. Heerlen, NL); or thermoplastic vulcanizates (TPVs) (e.g. Santoprene TPV available from ExxonMobil, (Houston, Tex., USA)).

A coupling layer may be disposed on the patient side of the electrode. In one implementation, the coupling layer is attached to an adhesive ring that is configured to adhere the electrode to a patient's skin and the coupling layer to the electrode. The coupling layer may also be sandwiched between two adhesive rings. The coupling layer and adhesive ring together form a modular coupling assembly. The coupling assembly is generally configured to be disposable, i.e., to be discarded after a single use. The adhesive ring may include a pressure sensitive adhesive that releasably joins the coupling assembly to the non-conductive matrix outside of the area where the metal component protrudes through the non-conductive matrix. The perimeter of the adhesive ring may correspond to the perimeter of the composite that is outside the treatment area 115 (sec FIG. 1A), which, in some implementations may be about ¾ of an inch wide. It is noted that the adhesive ring may function, in this respect, as a mask around the treatment area. In one implementation the adhesive ring can be comprised of 5 mil low density polyethylene (LDPE) (DV216-127A available from Lohmann Therapy Systems, West Caldwell, N.J.) or ¹⁄₃₂ inch polyethylene (PE) foam (Part No. 22116 also available from Lohmann Therapy Systems). Both the LDPE and PE as provided from Lohmann Therapy Systems are coated with a medical grade pressure sensitive adhesive (MTC 611 solvent based acrylic adhesive). In an alternative, coupling layer may be sandwiched between the above disclosed LDPE layers or PE layers or combinations thereof. After a used coupling assembly is removed, it can be replaced by a new one, allowing the composite structure to be re-used. The composite structure may be used for 100 uses or more providing for significant cost savings over pre-existing electrodes. Accordingly, the adhesive and non-conductive matrix materials should be selected so as to provide sufficient adhesion to the non-conductive matrix, but minimize residue on the non-conductive matrix after removal of the coupling assembly, to allow for re-use of the electrode. A coupling assembly may have a removable release sheet on one or both sides to protect the coupling layer prior to use.

Figure 6A:
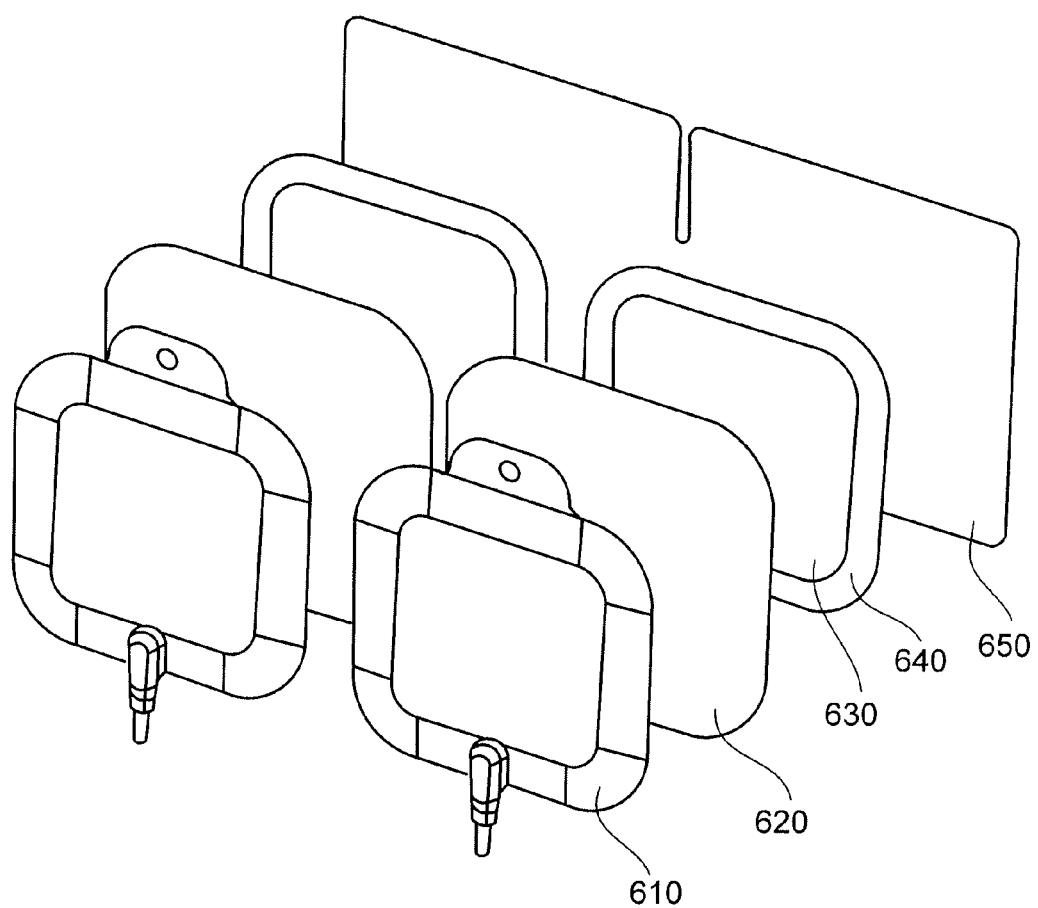
FIG. 6A-6C are illustrations of how a coupling layer can be connected to a composite structure.
Figure 6B:
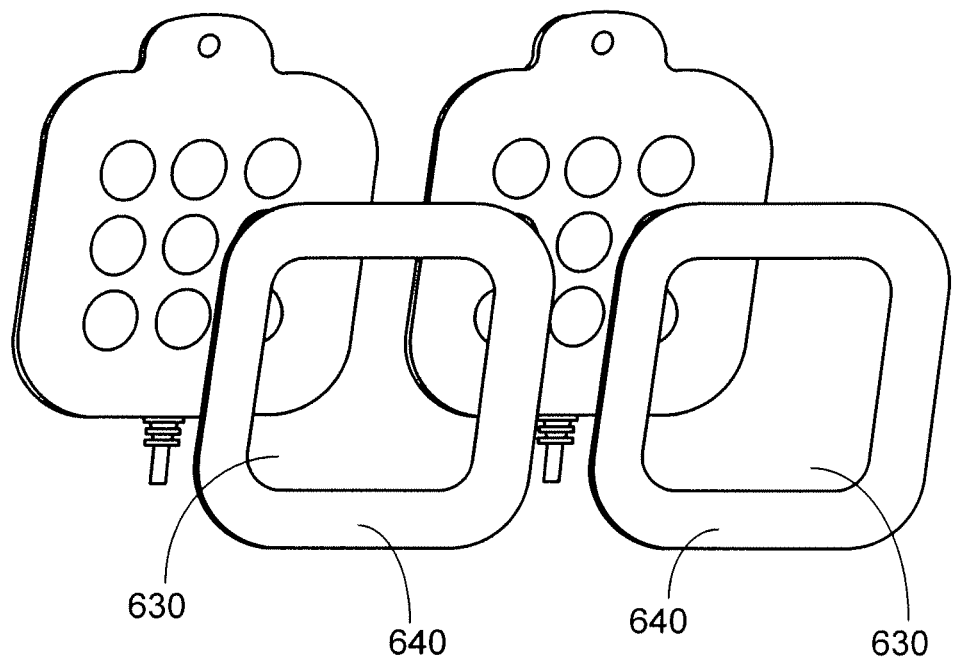
Figure 6C:
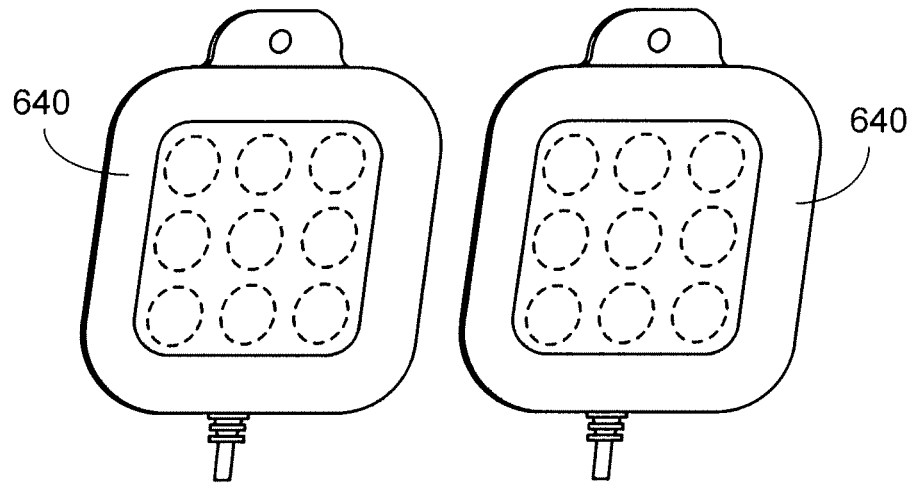

FIGS. 6A-6C illustrate the above in greater detail. FIG. 6A shows an exploded view of an electrode prior to attachment of the coupling assembly. In particular, coupling layer 630 is attached to adhesive ring 640, then sandwiched between removable liners (also referred to as release sheets) 620 and 650. The sandwich structure allows for separate packaging of the coupling assembly, which allows for the coupling assembly to be purchased separately (as a disposable item) from the composite structure which, as indicated above, may be reusable. In practice, the disposable coupling assembly is removed from its packaging, liner 620 is removed, and the adhesive ring carrying the coupling layer is adhered to the composite structure. Liner 650 is them removed and the electrode is attached to the patient.

The coupling layer may be any type of electrolyte (or other conductive material) in gel or liquid form, and may be optionally attached to a carrier. In some implementations the coupling layer comprises a high viscosity electrically conductive gel (often referred to as a "solid" gel) or hydrogel. Such hydrogels may include FW340 hydrogel (available from First Water Ltd., Wilshire, UK); AG604 hydrogel (available from Axelgaard Manufacturing Co., Fallbrook, Calif.); and RG63T hydrogel (available from Ludlow Manufacturing, Chicopee, Mass. Alternatively, a foam, cloth or sponge layer saturated with an electrically conductive liquid (e.g. saline) or gel may be used. When an electrode is to be used for cardiac pacing, an additional metallic material, (such as tin) should be added to the coupling layer between the electrolyte and the surface of the composite.

In another implementation, the adhesive ring is omitted and the coupling layer may be directly attached to the treatment area of the electrode. In an alternative implementation, liquid gel could be applied either directly on the electrode or directly on the patient prior to placing the electrode on the patient. Tape could then be used to attach the electrode to the body.

The electrodes described herein may be configured to be a multi-purpose defibrillator electrode, i.e., capable of monitoring electrical signals from the patient, as well as delivering defibrillation, pacing and cardioversion. For example, after a defibrillating pulse is delivered, the electrode is configured to monitor a signal that can be used to generate an ECG.

An additional implementation is illustrated in FIGS. 7A-7C. Note that the perspective on these Figures is from the non-patient side of the electrode. As such, the ghost outlines in FIG. 7A of the metal component and wire bundles is for illustrative purposes only. In this implementation, (see FIGS. 7A and 7B), a sternum electrode 700 having the characteristics described above, and configured for one or more of electrical signal monitoring, ECG monitoring, defibrillation, pacing and/or cardioversion is connected a sensor (or sensors) 710 constructed to acquire data indicative of the depth and rate of CPR compressions. The sensor can be one or more of an accelerometer or force and pressure monitors. The system is enabled to provide CPR feedback (in one mode in real time) to a caregiver. The functionality of the electrode and an accelerometer is as described in US Patent Application Publication 2006/0009809, the disclosure of which is herein incorporated by reference. The CPR sensor may be molded together with the composite structure using the molding processes describe above. The wiring 720 necessary for the CPR feedback functionality can be molded into the non-conductive matrix material connecting the sensor 710 to the electrode 700, and bundled with the high voltage wiring 730 for connection via combination bundle 740 to a defibrillator (not shown). It is noted for the purposes of this implementation, that the apex electrode 780 illustrated in FIG. 7C does not have the additional CPR feedback functionality.

Figure 8:
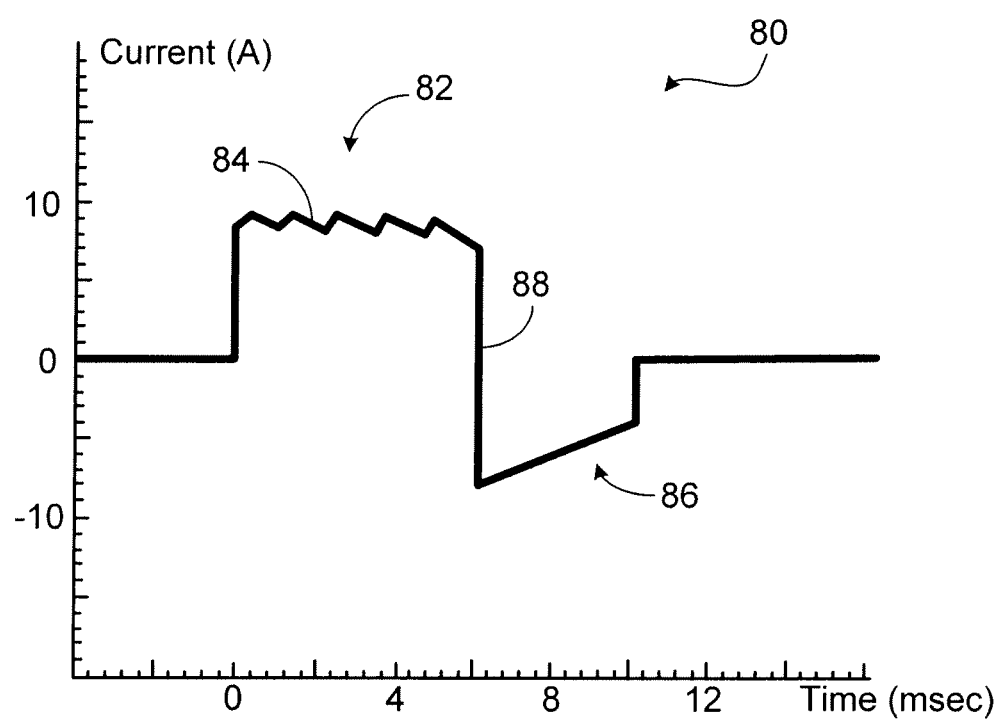
FIG. 8 is a waveform that may be used in conjunction with the electrodes of the invention.

As indicated above, the electrodes described hereinabove may be used with any type of waveform known in the art. One such waveform is a biphasic waveform. An example of a biphasic waveform is shown in FIG. 8. The biphasic waveform 80 shown in FIG. 8 includes a generally rectilinear positive phase 82 having a sawtooth ripple 84. The current of the positive phase is approximately 9 amps. The positive phase has a duration of approximately 6 milliseconds. The positive phase is followed by a negative phase 86. The negative phase has a duration of approximately 4 milliseconds and has an initial current of approximately −8 amps. The transition 88 between the positive and negative phases is generally very short, e.g., 0.1 millisecond or less.

The waveform shown in FIG. 8 is simply one example of a suitable waveform. Other waveforms having different characteristics may be used, including both biphasic waveforms having other shapes and other types of waveforms. It is preferred that the waveform used in conjunction with the herein described electrode is capable of depolarizing the electrode (i.e., either completely depolarizing the electrode or reducing the polarization to a level where a clean ECG can be obtained) within a few seconds, e.g., 4-6 seconds or less, after the pulse is delivered as described in US Patent Application Publication 2008/0221631 noted above. This allows the rescuer to continue treatment on a patient without interruption.

Figure 9:
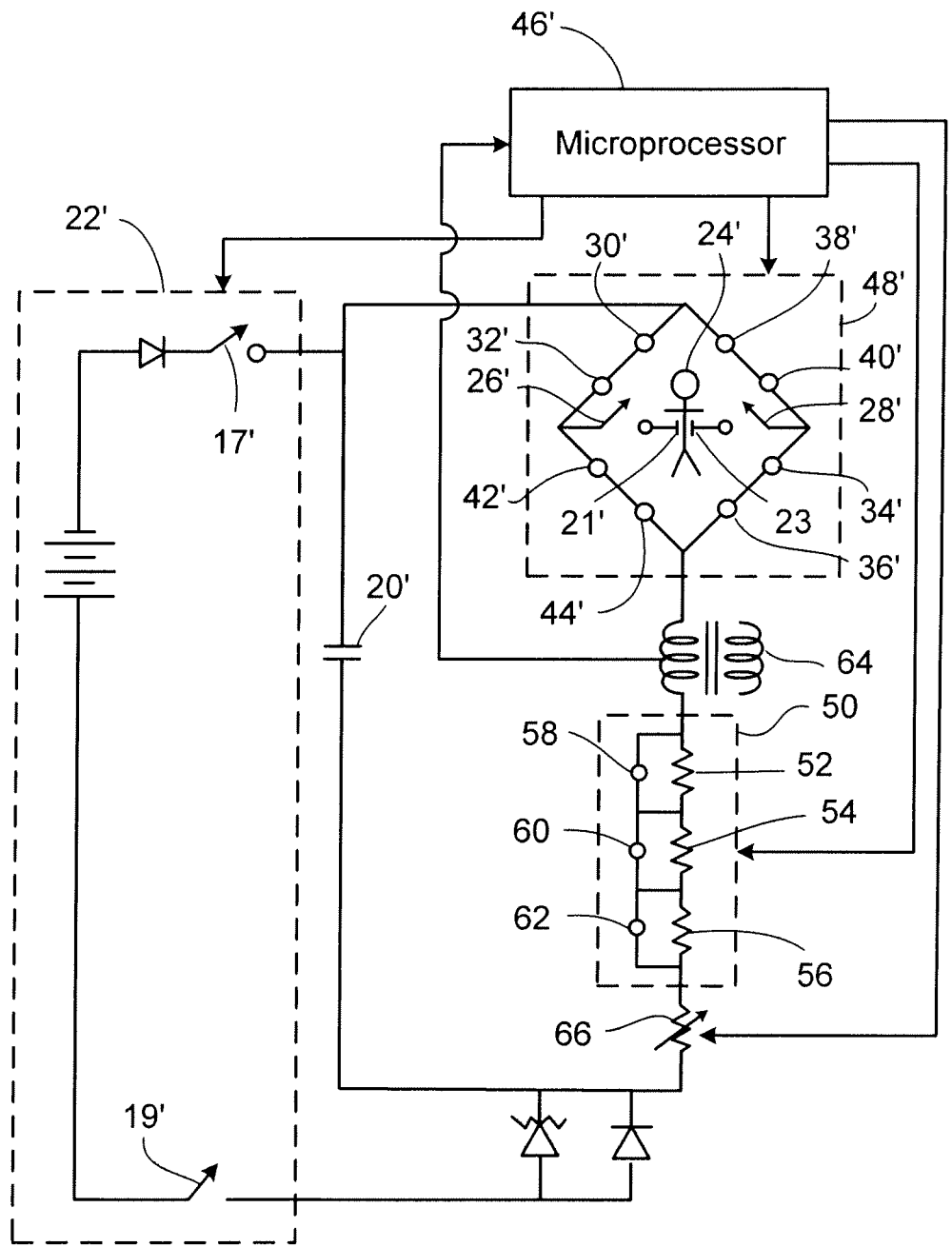
FIG. 9 is a diagram of a circuit suitable for generating the waveform of FIG. 8.

The waveform may be generated in any desired manner, e.g., using the circuitry described in U.S. Pat. No. 5,769,872. Referring to FIG. 9 herein, which is a reproduction of FIG. 2 of U.S. Pat. No. 5,769,872, a storage capacitor 20' (115 µF) is charged to a maximum of 2200 volts by a charging circuit 22' while relays 26' and 28' and the H-bridge are open, and then the electric charge stored in storage capacitor 20' is allowed to pass through electrodes 21' and 23' and the body of a patient 24'. In particular, relay switches 17' and 19' are opened, and then relay switches 26' and 28' are closed. Then, electronic switches 30', 32', 34', and 36' of H-bridge 48' are closed to allow the electric current to pass through the patient's body in one direction, after which electronic H-bridge switches 30', 32', 34', and 36' are opened and H-bridge switches 38', 40', 42', and 44' are closed to allow the electric current to pass through the patient's body in the opposite direction. Electronic switches 30'-44' are controlled by signals from respective opto-isolators, which are in turn controlled by signals from a microprocessor 46', or alternatively a hard-wired processor circuit. Relay switches 26', and 28', which are also controlled by microprocessor 46', isolate patient 24' from leakage currents of bridge switches 30'-44', which may be about 500 micro-amps. Relay switches 26' and 28' may be relatively inexpensive because they do not have to "hot switch" the current pulse. They close a few milliseconds before H-bridge 48' is "fired" by closure of some of the H-bridge switches.

Optionally, a resistive circuit 50 that includes series-connected resistors 52, 54, and 56 is provided in the current path, each of the resistors being connected in parallel with a shorting switch 58, 60, and 62 controlled by microprocessor 46. The resistors are of unequal value, stepped in a binary sequence to yield $2^n$ possible resistances where n is the number of resistors. During the initial "sensing pulse," when H-bridge switches 30', 32', 34', and 36' are closed, all of the resistor-shorting switches 58, 60, and 62 are in an open state so that the current passes through all of the resistors in series. Current-sensing transformer 64 senses the current passing through the patient 24', from which microprocessor 46 determines the resistance of the patient 24'.

Other implementations of the invention are within the scope of the claims.

The invention claimed is:

1. A reusable component of a hands-free defibrillation electrode, the reusable component comprising:
    a flexible nonconductive element, and
    a flexible reusable metallic element supported by the flexible nonconductive element and configured to spread current from a defibrillation shock across a treatment area large enough for defibrillation, at least 15 cm$^2$,
    wherein the flexible metallic element comprises a plurality of substantially inflexible metallic elements interconnected by flexible metallic linking elements,
    wherein the flexible nonconductive element comprises a flexible nonconductive material substantially encapsulating the metallic element except for a plurality of openings in the nonconductive material through which the substantially inflexible metallic elements are exposed on an active surface of the reusable component,
    wherein the active surface is configured to be adhered to a disposable coupling portion, and
    wherein the reusable component is sized and configured to accept an electrical defibrillation pulse and spread the electrical pulse to each of the exposed metallic elements, from which it is delivered through the openings in the nonconductive to the treatment area of the patient's chest through the disposable coupling portion, and
    wherein the reusable component is configured to be reused multiple times, each time with a new disposable coupling portion having been applied to the active surface of the reusable component.

2. The reusable component of claim 1 combined with a flexible disposable coupling portion to form a defibrillation electrode wherein the flexible disposable coupling portion comprises a conductive layer configured to be in electrical contact with the chest of the patient on one of its surfaces and in electrical contact with the active surface of the flexible reusable component on the other of its surfaces.

3. The defibrillation electrode of claim 2 wherein the reusable component and disposable portion are configured to be stored as separate elements, and to be adhered together when used to defibrillate a patient.

4. The electrode of claim 2 wherein the reusable component and disposable portion when adhered together form an electrode capable of being flexed simultaneously in more than one direction of curvature in order to conform to the shape of the patient's chest.

5. The electrode of claim 2 wherein the conductive layer of the coupling portion comprises a conductive viscous liquid.

6. The electrode of claim 5 wherein the conductive viscous liquid comprises an electrolyte.

7. The electrode of claim 2 wherein the conductive layer of the coupling portion comprises a solid conductive gel.

8. The electrode of claim 7 wherein the conductive layer comprises hydrogel.

9. The electrode of claim 2 wherein the disposable coupling portion includes a first peripheral adhesive region configured to adhere to the periphery of the reusable component.

10. The electrode of claim 9 wherein the disposable coupling portion includes a second peripheral adhesive region on the surface opposite the surface carrying the first peripheral adhesive region, and the second peripheral adhesive region is configured to adhere to the chest of the patient.

11. The electrode of claim 10 wherein the first and second peripheral adhesive regions are generally peripherally outside of the area through which electrical current flows from the exposed surface of the reusable component through the conductive layer of the coupling portion to the chest of the patient.

12. The electrode of claim 10 further comprising first and second release liners that, prior to assembly of the coupling portion to the reusable component, cover the first and second peripheral adhesive regions, respectively.

13. The electrode of claim 9 wherein the conductive layer of the coupling portion comprises a solid conductive gel with adhesive properties sufficient to adhere the coupling portion to the chest of the patient.

14. The electrode of claim 13 further comprising first and second release liners, and wherein, prior to assembly of the coupling portion to the reusable component, the first release liner covers the first peripheral adhesive region and the second release liner covers the solid conductive gel.

15. The reusable component of claim 1 wherein the flexible metallic linking elements are narrower than the substantially inflexible metallic elements.

16. The reusable component of claim 1 wherein the substantially inflexible metallic elements and flexible metallic linking elements are cut from the same sheet of metal.

17. The reusable component of claim 16 wherein the flexible metallic element is made from stainless steel.

18. The reusable component of claim 1 wherein the flexible metallic element is made from stainless steel.

19. The reusable component of claim 1 wherein the flexible nonconductive element comprises an elastomeric material.

20. The reusable component of claim 1 wherein the reusable component is combined with a sensor that provides an output from which information about the depth of CPR chest compressions can be obtained.

21. The reusable component of claim 20 wherein the sensor comprises an accelerometer.

22. The reusable component of claim 1 wherein the reusable component is combined with a sensor that provides an output from which information about the force applied to the chest during CPR chest compressions can be obtained.

23. The reusable component of claim 1 wherein the reusable component is combined with a sensor that provides an output from which information about the rate of CPR chest compressions can be obtained.

24. The electrode of claim 1 wherein each of the plurality of exposed metallic areas project beyond the surface of the surrounding nonconductive element.

* * * * *